United States Patent [19]

Beller et al.

[11] Patent Number: 5,792,878
[45] Date of Patent: Aug. 11, 1998

[54] PROCESS FOR PREPARING CHIRAL EPOXIDES USING CHIRAL MANGANESE TRIAZANONANE COMPLEXES AS OXIDATION CATALYSTS

[75] Inventors: Matthias Beller, Idstein; Ahmed Tafesh, Kelkheim; Richard Walter Fischer, Bad Soden; Bernd Scharbert, Frankfurt, all of Germany

[73] Assignee: Hoechst Aktiengesellschaft, Germany

[21] Appl. No.: 671,958

[22] Filed: Jun. 28, 1996

[30] Foreign Application Priority Data

Jun. 30, 1995 [DE] Germany ............... 195 23 890.7

[51] Int. Cl.[6] ............................................. C07D 301/12
[52] U.S. Cl. .................. 549/524; 549/525; 549/529; 549/531; 549/533
[58] Field of Search ..................... 549/524, 525, 549/529, 531, 533

[56] References Cited

FOREIGN PATENT DOCUMENTS 0 342 615  11/1989  European Pat. Off. .
0 544 519   6/1993  European Pat. Off. .
0 618 202  10/1994  European Pat. Off. .
  618202   10/1994  European Pat. Off. .

OTHER PUBLICATIONS

Journal of the America Chemical Society; Bd. 112, 1990, pp. 2801–2803; W Zhang et al: "Enantioselective epoxidation of unfunctionalised olefins catalysed by (salen)manganese complexes".

Journal of the America Chemical Socity; Bd. 113, 1991, pp. 7063–7064; E Jacobsen et al: "Highly enantioselective epoxidation catalysts derived from 1,2–diaminocyclohexane".

Irie, R., et al, *Tetrahedron Letters* 31:7345–7348 (1990).
Zhang, W., et al, *J. Am. Chem. Soc.* 112:2801–2803 (1990).
Jacobsen, E. N., et al, *J. Am. Chem Soc.* 113:7063–7064 (1991).
Hosoya, N., et al. *SYNLETT*:641–645 (1993).

*Primary Examiner*—Alan L. Rotman
*Assistant Examiner*—Lyman H. Smith
*Attorney, Agent, or Firm*—Connolly & Hutz

[57] ABSTRACT

A process for preparing chiral epoxides using chiral manganese triazanonane complexes as oxidation catalysts. These catalysts have the general formula $$[Mn_a(L)_z(OR)_w(\mu O)_x(\mu OAc)_y ]X_z] \tag{III}$$

17 Claims, No Drawings

PROCESS FOR PREPARING CHIRAL EPOXIDES USING CHIRAL MANGANESE TRIAZANONANE COMPLEXES AS OXIDATION CATALYSTS

Process for preparing chiral epoxides using chiral manganese triazanonane complexes as oxidation catalysts Stereoselective oxidation reactions are of central importance for the synthesis of a large number of active compounds and active compound intermediates for pharmaceuticals and agrochemicals. Epoxidation reactions in particular are an important method of preparing chiral compounds owing to the variety of ways in which the products can be functionalized.

Up to now there is no general process which enables epoxides to be obtained both in high yields and high enantioselectivities. The best catalyst systems existing at present for the enantioselective epoxidation of olefins to give epoxides are chiral manganese-salen complexes which were first described by Jacobsen et al. (J. Am. Chem. Soc. 1990, 112, 2801; J. Am. Chem. Soc. 1991, 113, 7063) and were later modified by Katsuki et al. (Synlett, 1993, 641; Tetrahedron Lett. 1990, 31, 7345). The class of manganese-salen catalysts is not generally suitable for industrial use. A great disadvantage of the Mn-salen complexes described is that the selectivity of the reaction is satisfactory only for cis olefins. For all other classes of olefins, the enantioselectivity is technically insufficient for practical use.

Furthermore, particularly from an industrial point of view, it is unsatisfactory that all catalyst systems known hitherto have only extraordinarily poor catalyst turnover numbers so that large amounts of catalyst, generally 5–10 mol %, have to be used.

For the above reasons, there was great industrial interest in finding improved processes for the enantio-selective oxidation of olefins which avoids the disadvantages described for preparing chiral epoxides and enables epoxides to be obtained in high yields and with high enantioselectivities.

The object is achieved by a process for preparing epoxides of the formula (I)

$$R^{1a}\underset{R^{2a}}{\overset{O}{\diagdown}}\underset{R^{3a}}{\overset{R^{4a}}{\diagup}} \quad (I)$$

where $R^{1a}$ to $R^{4a}$ are, independently of one another, hydrogen, $(C_1-C_{12})$alkyl, $(C_3-C_{12})$cycloalkyl, $(C_6-C_{12})$-bicycloalkyl, $(C_1-C_{12})$alkenyl, $(C_3-C_{12})$cycloalkenyl, $(C_1-C_{12})$alkynyl, alkoxy($C_1-C_{12}$), O-aryl, aryl, heteroaryl, $NH(C_1-C_{12})$alkyl, $N(C_1-C_{12})$ (alkyl)$_2$, halogen, where $R^{1a}$ and $RR^{2a}$, $RR^{2a}$ and $R^{3a}$, $RR^{2a}$ and $R^{4a}$ or $R^{3a}$ and $R^{4a}$ can together also form a ring, by reacting olefins of the formula (II)

$$R^{1a}\underset{R^{2a}}{\diagdown}\underset{R^{3a}}{\diagup}R^{4a} \quad (II)$$

where $R^{1a}$ to $R^{4a}$ are as defined above, with an oxidizing agent, wherein use is made as catalyst of a chiral manganese compound of the formula (III)

$$[Mn_u(L)_v(OR)_w(\mu O)_x(\mu OAc)_y]X_z \quad (III)$$

where:

u, v=1 or 2;

w, x, y=0, 1, 2 or 3;

z=1, 2 or 3;

with the proviso that if u=1, then v=1, w=1, 2, z=1, 2, 3, or if u=2, then v=2, w=0, 1, x=1, y=2, z=1, 2, or v=2, w=0, 1, x=1, y=2, z=2, 3, or v=2, w=0, 1, x=3, y=0, z=1, 2;

R is $(C_1-C_{12})$alkyl,

X is $PF_6^\ominus$, $F^\ominus$, $Cl^\ominus$, $Br^\ominus$, $I^\ominus$, $(C_6H_5)B^\ominus$, $ClO_4^\ominus$ and L is a chiral organic triazanonane ligand of the formula (II)

$$\text{(II structure with } R^1 \text{ to } R^{15} \text{ substituents on triazanonane backbone)}$$

where $R^1$ to $R^{12}$ are independently of one another, hydrogen, $(C_1-C_{12})$alkyl, $(C_3-C_{12})$cycloalkyl, $(C_1-C_{12})$alkenyl, $(C_1-C_{12})$alkoxy, $(C_1-C_{12})$acyloxy, aryl, heteroaryl, $CH_2$-aryl, COOH, COO($C_1-C_{12}$)alkyl, COO-aryl, CN, halogen, C-(halogen)$_3$, $NH_2$, $NH(C_1-C_{12})$alkyl, $N(C_1-C_{12}$-alkyl)$_2$, NH-aryl, N(aryl)$_2$, N-alkylaryl, $S(C_1-C_{12})$alkyl, $SO(C_1-C_{12})$-alkyl, $SO_2(C_1-C_{12})$alkyl, $P(C_1-C_{12}$alkyl)$_2$ and $R^{13}$ to $R^{15}$ are hydrogen, $(C_1-C_{12})$alkyl, $CH_2$-aryl, aryl and heteroaryl.

The process is of interest for preparing compounds of the formula (I) in which $R^{1a}$ to $R^{4a}$ are hydrogen, $(C_1-C_6)$-alkyl, $(C_3-C_7)$cycloalkyl, $(C_6-C_{12})$bicycloalkyl, $(C_1-C_6)$-alkenyl, $(C_3-C_7)$ cycloalkenyl, alkoxy-$(C_1-C_{12})$, aryl, heteroaryl or the pinane skeleton. Aryl and heteroaryl can be, for example, phenyl, benzyl, pyridyl, naphthyl or bipyridyl. Interesting preparations are, for example, those of compounds where formula (I) represents the following structures:

(three epoxide structures with substituents $R^{5a}$, $R^{6a}$, $R^{7a}$ shown)

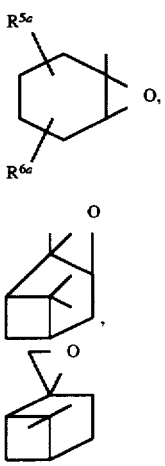

where $R^{5a}$, $R^{6a}$, $R^{7a}$ are hydrogen, $(C_1-C_5)$alkyl, $(C_1-C_6)$ alkoxy or halogen. The process is of particular interest for preparing products of the formula (I) where the target compound is styrene epoxide, a substituted styrene epoxide such as 3-chlorostyrene epoxide, trans-β-methylstyrene epoxide, indene epoxide, a 3-aryl epoxyallyl ether such as p-(2-methoxyethyl)phenyl epoxyallyl ether or epoxychromane, a substituted epoxychromane or cyclohexene epoxide or epoxypinane or carvone epoxide.

Particular importance attaches to compounds of the formula (I) in which 1 or 2 substituents are preferably hydrogen and the remaining substituents are as defined above.

Oxidizing agents which can be used are hydrogen peroxide, alkyl or arylalkyl hydroperoxides, bisalkyl peroxides, atmospheric oxygen in the presence of aldehydes, alkali metal or alkaline earth metal hypochlorites or periodates, amine oxides or per-acids. Good results are given by, for example, hydrogen peroxide, tert-butyl hydroperoxide, bis-tert-butyl peroxide, sodium hypochlorite, sodium periodate, idosobenzene or pyridine N-oxide.

Solvents used are generally inert organic solvents, with suitable examples being tert-butanol, methanol, tetrahydrofuran, toluene, ethyl acetate or acetic acid. It is also possible to carry out the process in solvent mixtures or multiphase systems. The manganese complexes used as catalyst are described in the application p 1952389.5-09 filed on the same day.

The manganese catalysts used are generally synthesized and isolated before the actual reaction, but in certain cases they can also be produced in situ.

The process is generally carried out at temperatures of 0°–100° C. Temperatures which have been found to be useful are from 20° to 80° C., in particular from 30° to 60° C.

It has been found useful to use from 1.0 to 2.0 mol, in particular from 1.05 to 1.8 mol, preferably from 1.1 to 1.7 mol, of oxidizing agent per double bond equivalent of alkene and to work at a pH of from 1 to 12, in particular from 4 to 10.

The following examples illustrate the process of the invention, without restricting it to them.

GENERAL PROCEDURES

1) Preparation of the Oxidation Solutions 100 ml of tert-butanol are admixed with 25 ml of 30% strength $H_2O_2$ (analytical reagent grade) and subsequently stirred for one hour with 30 g of anhydrous $MgSO_4$. The magnesium sulfate is then filtered off. The oxidation solution thus obtained is stored under refrigeration (−10° C.) as a precaution. Oxidizing agents which can be used as an alternative to hydrogen peroxide while maintaining comparable conversion figures are tert-butyl hydroperoxide, bis-tert-butyl peroxide (in each case dissolved in hydrocarbons), sodium hypochlorite (NaOCl), N-oxides (e.g. pyridine N-oxide), idosobenzene or periodates (e.g. $NaIO_4$).

2) Preparation of the Catalyst Solutions 20 mmol in each case of one of the catalysts A to D are added to 50 ml of the above-described oxidation solution. After the catalytically active compound has dissolved, this gives generally clear, sometimes yellowish solutions which keep for long periods of time at 0° C. At this temperature, the hydrogen peroxide decomposition caused by the catalyst is only slight (less than 0.5% decomposition within 7 days).

3) Catalytic Oxidation of Alkenes

The catalyst solution prepared according to points 1) and 2) is admixed with the alkene concerned (see Table 1); in the case of reactive olefins (cyclohexene, 2,3-dimethyl-but-2-ene), warming of the reaction mixture could be observed. The amount of alkene used corresponds, based on double bond equivalents, to between 60 and 90% of the molar amount of the hydrogen peroxide present in the catalyst solution. The oxidation reaction was generally complete after 1 hour (decrease in the catalyst activity). However, it was often found to be advantageous to carry out the oxidations over a period of about 18 hours, if desired at slightly elevated temperature (40°–50° C.), so as to achieve the conversions indicated. To remove the hydrogen peroxide still present, a catalytic amount of manganese dioxide $MnO_2$ is added to the reaction mixture with vigorous stirring. To remove the water formed, a superstoichiometric amount of $Na_2SO_4$ is then added after about 30 minutes, the mixture is stirred for 5–10 minutes and filtered through a glass frit covered with Celite (registered trademark of Manville Corp., Denver, USA). The filter residue is washed three times with a little THF. The combined filtrates are subsequently freed of the solvents under reduced pressure. The crude products thus obtained are further purified either by crystallization from customary solvents or distilled in the vacuum of a mercury diffusion pump (p<0.5 mbar) as gently as possible, i.e. without high thermal stressing.

pH of the oxidation reactions:

The pH of the catalyst solution reacted in each case can, individually matched to the requirements of the epoxides to be obtained, vary over a wide range (from 1 to 12), but preference is given to working in a pH range from 4 to 10. In each case it is advantageous to keep the water content of the reaction system low (e.g. to avoid an undesired ring opening of the epoxide or a loss in activity of the catalyst).

Use examples 1 to 12 are shown in Table 1, Table 2 indicates the ee values obtained.

Table 1 for epoxidation reactions

| Example | Starting material | Reaction conditions | Products | Yield cat. A in % | Yield cat. B in % | Yield cat. C in % | Yield cat. D in % |
|---|---|---|---|---|---|---|---|
| 1 | 1-Pentene | 30° C., 18 h | 1-Epoxypentane | 14 | 17 | 20 | 23 |
| 2 | cis-2-Pentene | 30° C., 18 h | cis-2-Epoxypentane | 15 | 19 | 18 | 25 |
| 3 | trans-2-Pentene | 40° C., 18 h | trans-2-Epoxypentane | 10 | 12 | 11 | 17 |
| 4 | 2,3-Dimethylbut-2-ene | RT, 1 h | 2,3-Dimethyl-2,3-epoxybutane | 32 | 22 | 35 | 42 |
| 5 | Cyclohexene | RT, 2 h | Epoxycyclohexane | 30 | 28 | 33 | 40 |
| 6 | Cyclooctene | RT, 2 h | Epoxycyclooctane | 25 | 31 | 45 | 56 |
| 7 | trans-4-Octene | RT, 18 h | trans-4-Epoxyoctene | 2 | 23 | 18 | 39 |
| 8 | 1,4-Cyclohexadiene | RT, 5 h | 1,2,4,5-bis-Epoxycyclohexane | 12 | 10 | 11 | 7 |
| 9 | Carvone | 50° C., 18 h | p-Menth-6-ene-8,9-epoxy-2-one | 25 | 11 | 23 | 18 |
| 10 | α-Pinene | RT, 3 h | exo-Epoxypinane | 12 | 13 | 22 | 27 |
| 11 | trans-β-Methylstyrene | RT, 18 h | trans-1,2-Epoxy-1-phenylethane | 19 | 13 | 26 | 29 |
| 12 | Chromane | RT, 18 h | Epoxychromane | 17 | 12 | 17 | 25 |

Catalyst concentration used: 0.5 mol %
Hydrogen peroxide ($H_2O_2$) concentration used: 5% by weight
Substrate concentration: 100 mol % based on catalyst used and from 60 to 70 mol % based on $H_2O_2$ used.

Table 2 for the enantioselctivity of the formation of the optically active epoxides produced using the chiral catalysts A–D:

| Example | Starting material | Reaction conditions | Products | ee in % cat. A | ee in % cat. B | ee in % cat. C | ee in % cat. D |
|---|---|---|---|---|---|---|---|
| 1 | Carvone | RT, 16 h | p-Menth-6-ene-8,9-epoxy-2-one | 43 | 55 | 32 | 30 |
| 2 | α-Pinene | 5° C., 20 h | exo-Epoxypinane | 58 | 48 | 44 | 51 |
| 3 | trans-2-Pentene | 40° C., 18 h | trans-2-Epoxypentane | 9 | 8 | 8 | 13 |
| 4 | Chromane | 12° C., 16 h | Epoxychromane | 72 | 78 | 68 | 80* |
| 5 | 4-(Methoxyethyl)-phenyl allyl ether | 20° C., 14 h | | 89 | 69 | 92 | 94 |

*ee was here from 85 to 90% when NaOCl or tert-butyl hydroperoxide was used as oxidizing agent in place of hydrogen peroxide.

We claim:

1. A process for preparing epoxides of the formula (I)

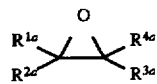   (I)

where $R^{1a}$ to $R^{4a}$ are, independently of one another, hydrogen, ($C_1$–$C_{12}$)alkyl, ($C_3$–$C_{12}$)cycloalkyl, ($C_6$–$C_{12}$)-bicycloalkyl, ($C_1$–$C_{12}$)alkenyl, ($C_3$–$C_{12}$)cycloalkenyl, ($C_1$–$C_{12}$)alkynyl, alkoxy($C_1$–$C_{12}$), O-aryl, aryl, heteroaryl, NH ($C_1$–$C_{12}$) alkyl, N($C_1$–$C_{12}$) (alkyl)$_2$, halogen, where $R^{1a}$ and $RR^{2a}$, $R^{2a}$ and $R^{3a}$, $R^{2a}$ and $R^{4a}$ or $R^{3a}$ and $R^{4a}$ can together also form a ring, by reacting olefins of the formula (II)

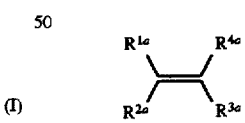   (II)

where $R^{1a}$ to $R^{4a}$ are as defined above, with an oxidizing agent, wherein use is made as catalyst of a chiral manganese compound of the formula (III)

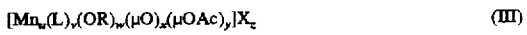   (III)

where:
u, v=1 or 2;
w, x, y=0, 1, 2 or 3;
z=1, 2 or 3;
with the proviso that if u=1, then v=1, w=1, 2, z=1, 2, 3, or
if u=2, then v=2, w=0, 1, x=1, y=2, z=1, 2, or
v=2, w=0, 1, x=1, y=2, z=2, 3, or v=2, w=0, 1, x=3, y=0, z=1, 2;

R is $(C_1-C_{12})$alkyl,

X is $PF_6^\ominus$, $F^\ominus$, $Cl^\ominus$, $Br^\ominus$, $I^\ominus$, $(C_6H_5)B^\ominus$, $ClO_4^\ominus$ and L is a chiral organic triazanonane ligand of the formula (II)

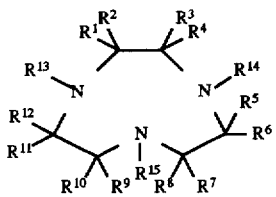

(II)

where

R$^1$ to R$^{12}$ are, independently of one another, hydrogen, $(C_1-C_{12})$alkyl, $(C_3-C_{12})$cycloalkyl, $(C_1-C_1)$alkenyl, $(C_1-C_{12})$ alkoxy, $(C_1-C_{12})$ acyloxy, aryl, heteroaryl, $CH_2$-aryl, COOH, COO$(C_1-C_{12})$alkyl, COO-aryl, CN, halogen, C(halogen)$_3$, $NH_2$, NH$(C_1-C_{12})$alkyl, N$(C_1-C_{12}$-alkyl)$_2$, NH-aryl, N(aryl)$_2$, N-alkylaryl, S$(C_1-C_{12})$alkyl, SO$(C_1-C_{12})$ alkyl, SO$_2(C_1-C_{12})$ alkyl, P$(C_1-C_{12}$alkyl)$_2$ and R$^{13}$ to R$^{15}$ are hydrogen, $(C_1-C_{12})$alkyl, $CH_2$-aryl, aryl and heteroaryl.

2. The process as claimed in claim 1, wherein R$^{1a}$ to R$^{4a}$ are, independently of one another, hydrogen, $(C_1-C_6)$alkyl, $(C_3-C_7)$cycloalkyl, $(C_6-C_{12})$bicycloalkyl, $(C_1-C_6)$alkenyl, $(C_3-C_7)$ cycloalkenyl, $(C_1-C_6)$alkoxy, phenyl, which can also be substituted by halogen, $(C_1-C_6)$alkyl, $(C_1-C_6)$alkoxy.

3. The process as claimed in claim 1, wherein 1 or 2 of the substituents R$^{1a}$ to R$^{4a}$ are hydrogen and the remainder are as defined above.

4. The process as claimed in claim 1, wherein formula (I) represents one of the following structures:

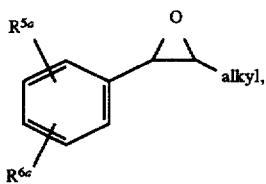

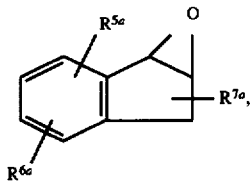

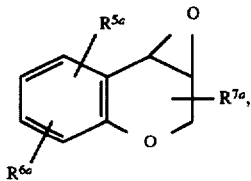

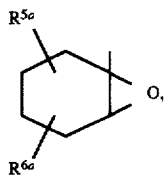

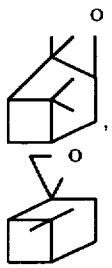

where R$^{5a}$, R$^{6a}$, R$^{7a}$ are hydrogen, $(C_1-C_5)$alkyl, $(C_1-C_6)$ alkoxy or halogen.

5. The process as claimed in claim 1, wherein the compound of the formula (I) is styrene epoxide, 3-chlorostyrene epoxide, trans-β-methylstyrene epoxide, indene epoxide, p-(2-methoxyethyl)phenyl epoxyallyl ether, epoxychromane, cyclohexene epoxide, epoxypinane or carvone epoxide.

6. The process as claimed in claim 1, wherein the oxidizing agent used is hydrogen peroxide, alkyl or arylalkyl hydroperoxides, bisalkyl peroxides, atmospheric oxygen in the presence of aldehydes, alkali metal or alkaline earth metal hypochlorites or periodates, amine oxides or peracids.

7. The process as claimed in claim 1, wherein the oxidizing agent used is hydrogen peroxide, tert-butyl hydroperoxide, bis-tert-butyl peroxide, sodium hypochlorite, sodium periodate, idosobenzene or pyridine N-oxide.

8. The process as claimed in claim 1, wherein inert organic solvents are used as solvent.

9. The process as claimed in claim 1, wherein from 1.0 to 2.0 mol of oxidizing agent are used per double bond equivalent of alkene.

10. The process as claimed in claim 1, wherein the reaction is carried out at a temperature of from 0° to 100° C.

11. The process as claimed in claim 1, wherein the reaction is carried out at a pH of from 1 to 12.

12. The process as claimed in claim 8, wherein the inert organic solvents are tert-butanol, methanol, ethyl acetate, tetrahydrofuran, toluene or acetic acid.

13. The process as claimed in claim 1, wherein from 1.04 to 1.8 mol of oxidizing agent are used per double bond equivalent of alkene.

14. The process as claimed in claim 1, wherein from 1.1 to 1.7 mol of oxidizing agent are used per double bond equivalent of alkene.

15. The process as claimed in claim 1, wherein the reaction is carried out at a temperature of from 20° to 80° C.

16. The process as claimed in claim 1, wherein the reaction is carried out at a temperature of from 30° to 60° C.

17. The process as claimed in claim 1, wherein the reaction is carried out at a pH of from 4 to 10.

* * * * *